(12) United States Patent
McCann et al.

(10) Patent No.: US 7,221,440 B2
(45) Date of Patent: May 22, 2007

(54) SYSTEM AND METHOD FOR CONTROLLING INK CONCENTRATION USING A REFRACTOMETER

(75) Inventors: James D. McCann, Waynesville, OH (US); Daniel J. DeVivo, Dayton, OH (US); Jeffrey S. Trapp, Kettering, OH (US)

(73) Assignee: Eastman Kodak Company, Rochester, NY (US)

( * ) Notice: Subject to any disclaimer, the term of this patent is extended or adjusted under 35 U.S.C. 154(b) by 386 days.

(21) Appl. No.: 10/896,462

(22) Filed: Jul. 22, 2004

(65) Prior Publication Data

US 2006/0044550 A1    Mar. 2, 2006

(51) Int. Cl.
    *G01N 21/41* (2006.01)
(52) U.S. Cl. ..................................... 356/128
(58) Field of Classification Search ................ 356/128, 356/445
    See application file for complete search history.

(56) References Cited

U.S. PATENT DOCUMENTS

| | | | |
|---|---|---|---|
| 3,669,545 A | 6/1972 | Gilby | |
| 4,382,656 A | 5/1983 | Gilby | |
| 4,730,882 A | 3/1988 | Messerschmidt | |
| 5,035,504 A | 7/1991 | Milosevic et al. | |
| 5,170,056 A | 12/1992 | Berard et al. | |
| 5,373,366 A * | 12/1994 | Bowers | 356/435 |
| 5,452,083 A | 9/1995 | Wilks, Jr. | |
| 5,694,210 A * | 12/1997 | Newell et al. | 356/128 |
| 5,835,231 A | 11/1998 | Pipino | |
| 6,067,151 A | 5/2000 | Salo | |
| 6,124,937 A | 9/2000 | Mittenzwey et al. | |
| 6,141,100 A | 10/2000 | Burka et al. | |
| 6,480,282 B1 | 11/2002 | Chinowsky et al. | |
| 6,504,651 B1 | 1/2003 | Takatori | |

(Continued)

FOREIGN PATENT DOCUMENTS

EP    0 671 622    7/2000

(Continued)

OTHER PUBLICATIONS

Refractive Index Sensor with a Guided-Mode Resonant Grating Filter, p. 219—Optical Engineerng for Sensing and Nanotechnology (ICOSN 2001), Koichi Iwata, Editor, Proceedings of SPIE vol. 4416 (2001), pp. 219-222.

(Continued)

*Primary Examiner*—Gregory J. Toatley, Jr.
*Assistant Examiner*—Kara Geisel
(74) *Attorney, Agent, or Firm*—The Buskop Law Group, P.C.

(57) ABSTRACT

The present invention relates to ink output in ink jet printing systems. A refractometer is used to control the concentration of inks used in continuous ink jet printers. A concentration detector measures the total amount of light reflected from a surface. Changes in the ink cause a definite change in sensor output. As the refractive index is changed, shifting the critical angle for internal reflection, more or less light is reflected to the sensor. The index of refraction can be determined from the sensor once corrections are made to account for temperature dependencies of the sensor and light source and baseline measurement of reflected light amplitude. These dependencies are carried out in the refractometer.

7 Claims, 3 Drawing Sheets

U.S. PATENT DOCUMENTS

| 7,064,816 B2 * | 6/2006 | Langenbacher et al. .... 356/128 |
| 2002/0149775 A1 | 10/2002 | Mori et al. |
| 2005/0007596 A1 | 1/2005 | Wilks, Jr. et al. |

FOREIGN PATENT DOCUMENTS

| EP | 0671622 | 12/2000 |
| WO | 88/01376 | 2/1988 |
| WO | 93/09421 | 5/1993 |

OTHER PUBLICATIONS

New Technique for Determining the Optical Constants of Liquids, by C. Dale Keefe and Jason K. Pearson, Society for Applied Spectroscopy, vol. 56, No. 7, 2002-09728.

Absorption Measurement using a Leaky Waveguide Mode, Optical Reiew vol. 4, No. 3 (1997) 354-357.

An Optical Fibre Refractometer for Liquids using Two Measurement Channels to Reject Optical Attenuation, J. Phys. E: Sci. Instrum. 21 (1988) (64-67).

Absorption Sensor Based on Total Internal Reflection Diffraction Grating, Institute of Physics Publishing, J. Opt. A: Pure Appl. Opt. 4 (2002) 382-386.

Design of a Proe for Sensing the Complex Index of Refraction of Liquids, Section 8: Industrial Applications of Sensors pp. 263-268 (Sep. 2001).

Optical Refractometer for Complex Refractive Index Measurement in UV-NIR Range, SPIE vol. 3730, pp. 118-121 (2003).

Internal Reflection Spectroscopy by N. J. Harrick, New York, Interscience Publishers [1967].

* cited by examiner

SYSTEM AND METHOD FOR CONTROLLING INK CONCENTRATION USING A REFRACTOMETER

TECHNICAL FIELD

The present invention relates to ink output in ink jet printing systems and, more particularly, to controlling the concentration of the ink output.

BACKGROUND ART

In a continuous ink jet fluid system, the ink used, which includes a carrier fluid, such as water or a solvent, and dye, is continuously recirculated through the system. As it is recirculated, it mixes with air in the return lines and is maintained under vacuum in the ink reservoir. Evaporation of the carrier fluid due to the air-ink interaction increases the dye concentration of the ink which changes various fluid properties such as viscosity and surface tension. Therefore the optimal parameters used to control the ink jet printing process change as the ink concentration varies. As would be obvious to one skilled in the art, affecting ink properties such as viscosity is detrimental, since the energy required to stimulate filaments is determined partially by the viscosity of the fluid.

Proper dye concentration is essential to the stable operation of an ink jet printhead. The measurement of dye concentration is used to determine the amount of replenisher needed to mix with the ink to compensate for the carrier fluid lost due to evaporation. When printing rates are high, the ink usage rate due to printing is much higher than loss rate due to evaporation, therefore the fluid system can be refilled with ink without significantly affecting the ink concentration.

Alternatively, when little or no printing is being done, the system is in an idle condition and the evaporation rate of the carrier fluid is typically higher than the amount of ink removed during printing. In this instance, then, the ink concentration level increases. A replenishment fluid is needed to bring the ink concentration level down to the proper mixture.

Maintaining ink concentration in a continuous ink jet printing system is known in the art. One prior art method for controlling the ink concentration involves counting the print drops. By knowing the number of drops printed and the typical drop size, derived from hole size, one has a measure of the amount of ink printed; the actuations of the float in the tank are used to determine the volume of fluid lost from the tank; the difference between the amount of fluid lost from the tank and the amount printed is assumed to be vehicle lost due to evaporation. Counting printed drops is an open loop control with no feedback parameters. This scheme is sensitive to the accuracy of the estimated drop volume. Small holes size errors or pressure variations can produce drop volumes larger or smaller than assumed by the control system. Ink losses due to spillage or leakage can also not be accounted for. As a result, this scheme can not maintain the ink concentration required for high print quality applications.

Ink concentration has also been monitored by means of the resistivity if the ink, as in patent U.S. Pat. No. 3,761,953 and European Patent No. 0597628A. Resistivity control also is not precise. The resistivity of the ink is not only affected by the ionic content of the dye but also by ions from impurities in the dye stuff and the ink vehicle. Temperature also affects resistivity and calibration curves are necessary to correlate the concentration and resistivity at various temperatures. Furthermore, the resistivity of the ink also changes with time after the ink has been initially installed in the system. As a result, resistivity is less than an ideal indicator of ink concentration.

Thus, these previous methods of concentration control are indirect and do not measure a property of the ink directly linked to concentration. Absorption of light by the ink is directly tied to the concentration of ink. U.S. Pat. Nos. 5,373,366 and 5,241,189 describe a method for monitoring the concentration of the ink by means of the optical absorption. Ink, being pumped to the printhead, passes through a optical cell consisting of closely spaced transparent glass walls. Light from an LED passes through the ink in the cell and is detected by a photodiode. The amount of light detected by the photodiode depends not only on the concentration of the ink but also on the thickness of the optical cell. For a highly absorbing black ink, a very thin optical cell must be used to allow sufficient light to be detected. The small gap through which the fluid must pass in the optical cell can result in unacceptably high pressure drops at the required flow rates.

To reduce the pressure drop, the width of the cell must be fairly large. The resulting large surface area of the optical plates makes the spacing of the optical plates sensitive to changes in ink pressure. As the absorption of the light in the cell varies exponentially with the spacing, the apparent concentration of the ink, as indicated by the optical absorption in the optical cell, varies with ink pressure.

The optical concentration sensor described in U.S. Pat. No. 5,241,189 uses an infrared light emitting diode. Not all dyes and pigment used in inks are absorbing in the IR. As a result, the '189 patent is not applicable for use with all inks. Even with a visible light spectrum, different inks, especially different color inks, have wildly different light absorption characteristics. To provide the desired ink concentration sensitivity for the different inks, one would need to use optical cells whose thickness must be matched to the ink of choice. This is not a practical option.

The optical concentration sensor described in commonly assigned, co-pending U.S. patent application Ser. No. 09/211,035, provides a novel optical cell which overcomes some of the shortcomings of the prior art optical cells. The optical cell walls comprise transparent cylindrical rods between which the fluid being tested passes. These rods can be positioned sufficiently close to each other that the transmission rate can be measured even for highly absorbing inks. The curvature of the glass rods rapidly increases the thickness of the optical cell away from the measurement zone so that the pressure drop produced by flow through the cell can be acceptably low. By varying the gap between the rods from end to end, this concentration sensor can provide small transmission cell thicknesses for testing fluids with high absorption rates and larger cell thicknesses for testing fluids with lower absorption rates.

SUMMARY OF THE INVENTION

This need is met by the system and method according to the present invention, wherein ink concentration is controlled using a refractometer. Any concentration control technique will necessarily rely heavily on an accurate measurement of dye concentration in a water solution. The present invention proposes using the index of refraction for an accurate measurement of dye concentration in an aqueous solution to control the ink concentration.

In accordance with one aspect of the present invention, a refractometer is used to control the concentration of inks used in continuous ink jet printers. A concentration detector measures the total amount of light reflected from a surface. Changes in the ink cause a definite change in sensor output. As the refractive index is changed, shifting the critical angle for internal reflection, more or less light is reflected to the sensor. The index of refraction can be determined from the sensor once corrections are made to account for temperature dependencies of the sensor and light source and baseline measurement of reflected light amplitude. These dependencies are carried out in the refractometer.

Other objects and advantages of the invention will be apparent from the following description, the accompanying drawings and the appended claims.

DETAILED DESCRIPTION OF THE INVENTION

Figure 1:
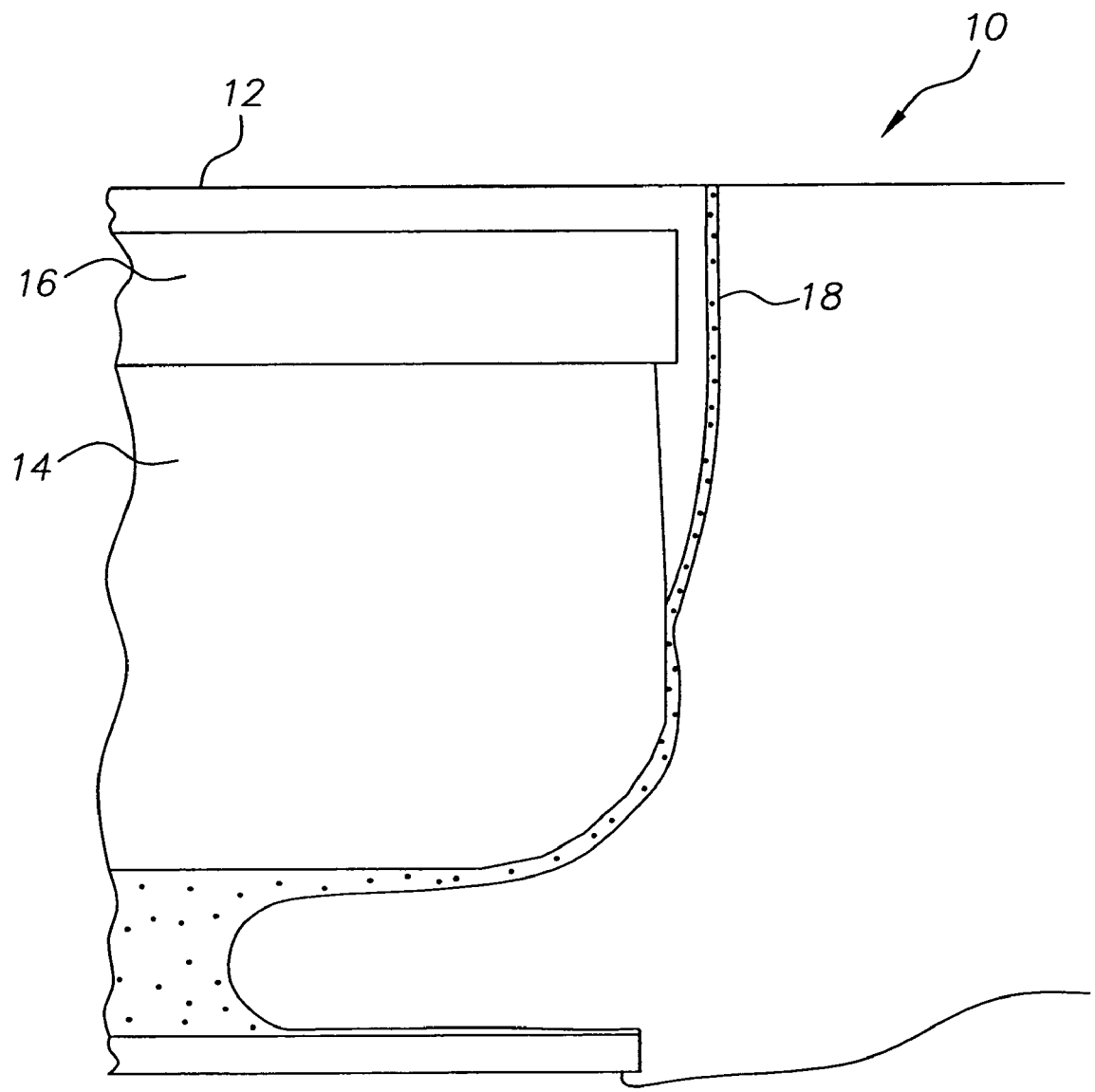
FIG. 1 is a block diagram of a typical printhead for a continuous ink jet printer, to which the teachings of the present invention are applicable.

Referring now to the drawings, in FIG. 1, there is illustrated a prior art view of a drop generator and catcher assembly 10. A drop generator 12 is situated in an area above a catcher 14 and charge plate 16. The printhead defines one or more rows of orifices which receive an electrically conductive recording fluid from a pressurized fluid supply manifold and eject the fluid in rows of parallel streams. Printers using such printheads accomplish graphic reproduction by selectively charging and deflecting the drops in each of the streams and depositing at least some of the drops on a print receiving medium. The uncharged ink droplets flow along a trajectory path indicated by 18 in FIG. 1.

In continuous ink jet printer operation, printhead life is critical for optimum operation. Proper function of the printhead is dependent on ink properties such as viscosity, surface tension and concentration. These properties affect satellite-free drop formation, drop breakoff phase, catcher film flow, charge voltage print window, condensation cleaning, dry shutdown, air ingestion, crossflow rate, foaming and carryover. The viscosity and surface tension of the ink is affected by the concentration, i.e. the amount of dye in the ink. In accordance with the present invention, improved concentration control is provided, positively affecting the printhead life.

The present invention provides for an ink concentration control technique for particular application with printheads for continuous ink jet printers. In many chemical processing applications, the refractive index of a liquid can be used to monitor the concentration of various constituents in liquids. Examples include food products, e.g. juices, concentrates, soft drinks and sucrose solutions. Industrial fluids range from gasoline to aircraft de-icing fluid. The use of refractive index has broad application and durability.

One convenient means to measure the index of refraction is based on the measurement of the critical angle for total internal reflection. When light strikes an interface between two materials some light is typically reflected back into the first material and some light is refracted into the second material. The relative amounts of light that are reflected and refracted depends on the index of refraction for both materials and on the angle of incidence of the light. When the first material has a higher refractive index than the second material, light passing through the first material and striking the interface at a more glancing angle than a critical angle, will be totally reflected back into the first material with no light propagating into the second material. This phenomena is know as total internal reflection. While all the light incident on the interface from the first material side, at angles of incident larger than the critical angle, is reflected at the material interface, for angles of incidence less than the critical angle less than half the light is reflected at the interface. As a result of total internal reflection, the amplitude of the reflected light as a function of the angle of the incident light with respect to the surface normal increases dramatically at the critical angle, making the detection of this critical angle quite simple.

The critical angle can be calculated as $$\Box = \sin^{-1}(n_2/n_1),$$

where $n_2$ is the index of refraction for the fluid being tested, $n_1$ is the index of refraction for the transparent wall in contact with the fluid, and $n_2 < n_1$. Changes in $n_2$, the refractive index of the fluid, therefore produce shifts in the critical angle. As $n_2$ increases, the critical angle $\Box$ increases, requiring the light to hit the interface at a greater, or more glancing, angle before total internal reflection is obtained.

Figure 2:
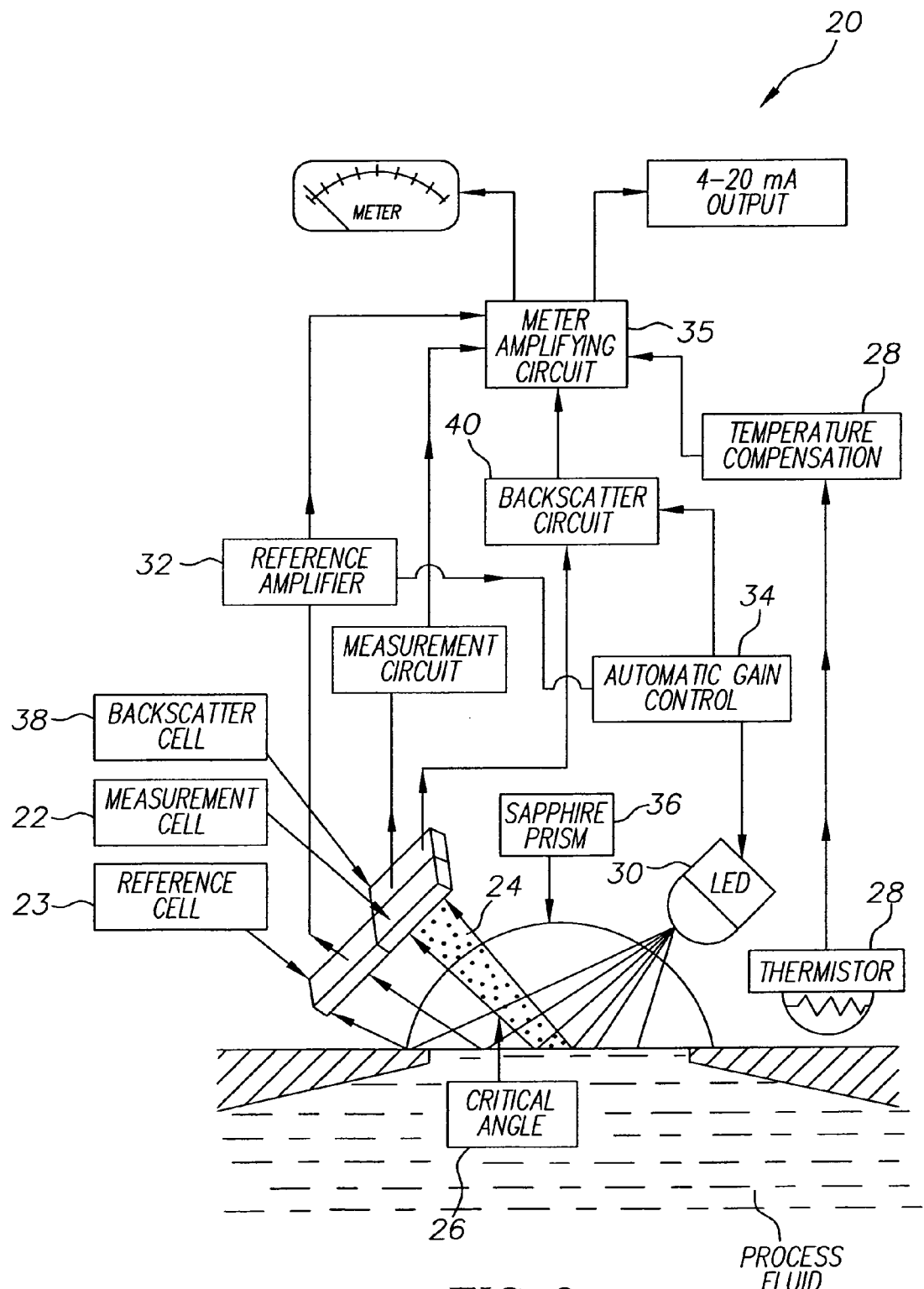
FIG. 2 is a schematic block diagram of a refractometer of the type suitable for controlling ink concentration, in accordance with the present invention.

In FIG. 2, there is illustrated a circuit diagram 20 for a concentration detector, such as a refractometer. Changes in the refractive index cause the critical angle to shift and, therefore, the amount of light that reaches the sensor, to change. In some commercial refractometers, the sensor comprises a CCD array, such as a 1-d video camera, that is able to measure the light profile down the length of the sensor. The concentration detector illustrated in FIG. 2, however, is a PR-111 refractometer commercially available from AFAB industries, and does not employ a CCD array or other such means for measuring the light profile. Rather, the refractometer illustrated in FIG. 2 uses a single sensor or measurement cell 22 to measure the total amount of light reflected from the surface through a range of reflection angles. The output of the measurement cell is proportional to the amount of light striking the measurement cell. As the refractive index is changed, the critical angle 26 for internal reflection is shifted, causing the amount of light detected by the measurement cell 22 to vary.

An LED 30 is the light source for the instrument. The light emitted from the curved lens of the LED 30 produces rapidly diverging beam of light, that is directing into the transparent prism 36. This transparent prism serves as a transparent wall in contact with the ink. This transparent prism must have an refractive index higher than that of the inks to be tested so that light directed through the prism to the interface with the ink will undergo total internal reflection if the angle of incidence (measured from the normal to the interface) is greater than a certain critical angle.

The prism 36 is typically made of sapphire ($Al_2O_3$), which has a high index of refraction and is chemically resistant to a wide range of fluids. As a result of the diverging nature of the beam of light from the LED, the light strikes the interface between the prism and the ink at a broad range of incident angles. This broad range of incident angles includes the critical angle for the onset of total internal reflection as well as a broad range of incident angles on both sides of the critical angle.

The measurement cell 22 is a photo detector to measure light reflected from the interface between the prism and the ink. This measurement cell is sized and positioned so that it detects light reflected from the ink-prism interface over a range of reflection angles that includes the critical angle 26 for total internal reflection. Changes in the critical angle 26, caused by changes in the refractive index of the ink, cause the amount of light reflected into the measurement cell 22 to vary. The output of the measurement cell 22 therefore varies in response to changes in the refractive index of the ink. The output of the measurement cell can also vary as a result of changes in the LED output or due to drifts in detector efficiency. The life of LED's is fairly well known, in that their light output will degrade in a semi-log fashion.

To minimize these variations in output, a reference cell 23 is used. This reference cell is positioned so that it receives light having reflection angles significantly greater than the critical angle for total internal reflection. At such angles, the amplitude of the reflected light is not affected by changes in the critical angle produced by changes in the refractive index of the ink. The output of the reference cell provides a measure of the LED output and the detector sensitivity. The output of the reference cell 23 can therefore be used in cooperation with reference amplifier means 32, automatic gain control means 34, and meter amplifying means 35 to reduce the sensitivity of the output to the drifts in LED and detector efficiency.

Continuing with FIG. 2, the thermistor and temperature compensation means 28 correct for temperature induced changes in output, due, for example, to temperature dependence of the LED and the measurement cell. A third detector, the backscatter cell 38, can also be employed to detect light scattered from particles in the fluid. This detector is positioned where it will detect such scattered light but not light reflected at the ink-prism interface. The output of the backscatter cell, after appropriate conditioning by the backscatter circuit 40, can be used to modify refractometer output for fluids where backscatter is significant.

The index of refraction can be determined from the sensor, once corrections are made to account for temperature dependencies of the sensor and light source and baseline measurement of reflected light amplitude. For the circuit of FIG. 2, these corrections are carried out by electronics associated with the refractometer. Alternatively, the outputs of the several sensors can be monitored by computer means and the corrections carried out though computer algorithm means.

Refractometers, such as that illustrated in FIG. 2, work well for measuring the refractive index of fluids that are not very light absorbing. However, when used with fluids that are strong light absorbers, the physics involved in the reflection of the light at the interface becomes quite complicated. The reflected amplitude is reduced for angles that should be totally reflected as a result of the optical absorption characteristics of the fluid. This phenomenon is known as attenuated total reflection. Attenuated total reflection can be used as one of the bases for concentration measurement. It is known in the art that the reflectivity drops as the absorption factor of the liquid increases. The absorbing medium strongly affects the reflectivity for internal reflection, particularly in the vicinity of the critical angle 26.

By appropriate analysis of the reflected amplitude vs. angle of reflection, one can obtain both the absorption factor for the fluid as well as its refractive index. Typical refractometers, including those with CCD arrays for measuring the entire reflection amplitude vs. reflection angle curve, do not provide sufficient analysis means to determine the refractive index and the absorption factor for highly absorbing liquids. A detector system like that illustrated in FIG. 2, does not make sufficient measurements of the reflection amplitude with respect to the angle to differentiate between changes in the measured light levels due to absorption properties of the fluid and those due to the refractive index of the fluid. If either the refractive index or the absorption factor of the ink were to increase, the amplitude of the light reflected into the measurement cell would decrease. In response to such a decrease in reflected light, the refractometer of FIG. 2 produces an output change indicative of an increase in the refractive index of the fluid. While it might be interesting from a research viewpoint to separately measure the absorption factor and the refractive index as a function of concentration, system control requirements only mandate that the measured response have sufficient amplitude change as a result of concentration.

Figure 3:
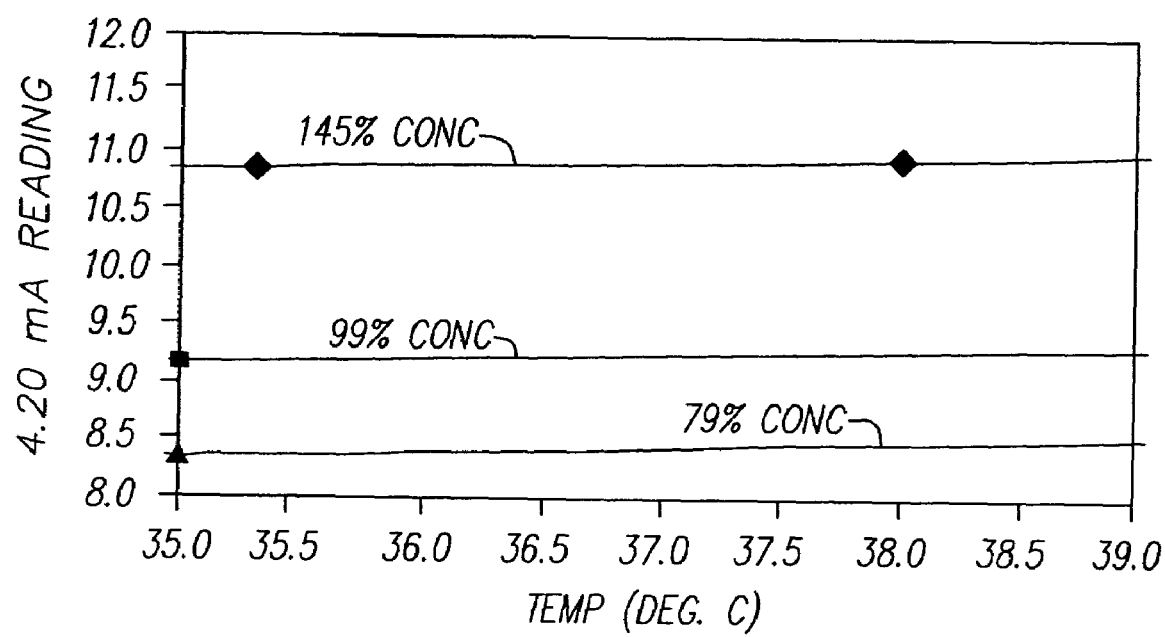
FIG. 3 is a graph illustrating the change in sensor output with changes in ink concentration.

Referring now to FIG. 3, there is a graph showing output signal levels from the refractometer as a function of ink concentration. This graph shows that even for a yellow ink, the least absorbing of the different color inks, there is significant change in the refractometer output with respect to concentration, to make the refractometer output a useful signal for control of the ink concentration. The output is temperature dependent, and must be accounted for to maintain the proper concentration. The output of the thermistor 28, located close to the prism 36 and thermally coupled to the prism, in concert with temperature compensation circuit means, is used to minimize the temperature dependence of the output.

When this concentration sensor is used in an ink jet printer, whenever the ink level is low in the ink reservoir, the concentration control system adds ink or replenishment fluid as needed to maintain the output from the concentration sensor at a fixed value. Depending on the color and darkness of each ink, each ink will have its own setpoint at which the concentration sensor output must be maintained. The temperature dependence of these setpoints can also vary for the different ink types. Hence, the actual control is accomplished by first determining when the ink level in the fluid is slightly low due to a "Level switch" or "float". Once such a determination is made, the concentration measuring means determines whether the ink is "high" in concentration or "low" in concentration. A valve would then be opened to allow fluid into the ink tank to satisfy the ink float. If concentration is "low", replenisher is added. If concentration is "high", ink is added. The amount added can be on the order of about 50 mL, with a system volume on the order of about 1500 mL. Thus, each addition of fluid would adjust concentration by about 3%.

Having described the invention in detail and by reference to the preferred embodiment thereof, it will be apparent that other modifications and variations are possible without departing from the scope of the invention defined in the appended claims.

The invention has been described in detail with particular reference to certain preferred embodiments thereof, but it will be understood that variations and modifications can be effected within the spirit and scope of the invention.

The invention claimed is:

1. An ink concentration measuring and control system comprising:

means for producing an interface between an ink and an optically transparent material, wherein the transparent material has an index of refraction higher than an index of refraction of the ink;

means for measuring the attenuated total reflection of light off the interface between the ink and the transparent material at a range of reflection angles that includes at least a critical angle for the attenuated total reflection;

means for measuring amplitude of a reference portion of light that includes light reflected from the interface at angles significantly greater than the critical angle for the attenuated total reflection; and means for producing an ink concentration related output from the measured attenuated total reflection.

2. A system as claimed in claim 1 wherein the means for determining the ink concentration comprises a comparison of an output to a target value.

3. An ink concentration measuring and control system for use with an ink having a concentration and an index of refraction, the system comprising:

an optically transparent wall having an index of refraction higher than the index of refraction of the ink, the optically transparent wall being in contact with the ink to provide an interface between the optically transparent wall and the ink;

light producing means for directing light through the optically transparent wall so that light is reflected off the interface;

light detector means for measuring amplitude of at least a portion of light reflected off the interface at a range of reflection angles that includes at least a critical angle for total internal reflection;

means for measuring amplitude of a reference portion of light from the light producing means, wherein the measured reference portion of light includes light reflected from the interface at angle significantly greater than the critical angle for total internal reflection; and means for determining the concentration of the ink from the measurement by said light detector means.

4. A system as claimed in claim 3 wherein the measured reference portion of light is used to improve stability of the ink concentration determining means.

5. An ink concentration measuring and control system for use with an ink having a concentration and an index of refraction, the system comprising:

an optically transparent wall having an index of refraction higher than the index of refraction of the ink, the optically transparent wall being in contact with the ink to provide an interface between the optically transparent wall and the ink;

a light source adapted to direct light through the optically transparent wall so that light is reflected off the interface;

a light sensor adapted to measure amplitude of at least a portion of light reflected off the interface at a range of reflection angles that includes at least a critical angle for total internal reflection;

a reference device adapted to measure amplitude of a reference portion of light from the light source, wherein the measured reference portion of light includes light reflected from the interface at angles significantly greater than the critical angle for total internal reflection; and an ink concentration determining device adapted to determine the concentration of the ink from the measurement by the sensor.

6. An ink concentration measuring and control system for use with an ink having a concentration and an index of refraction, the system comprising:

an optically transparent wall having an index of refraction higher than the index of refraction of the ink, the optically transparent wall being in contact with the ink to provide an interface between the optically transparent wall and the ink;

a light source adapted to direct light through the optically transparent wall so that light is reflected off the interface;

a light measurement device adapted to measure amplitude of at least a portion of light reflected off the interface at a range of reflection angles that includes a critical angle for total internal reflection;

a reference device adapted to receive light reflected from the interface at angles significantly greater than the critical angle for total internal reflection so that amplitude of the reflected light is not affected by changes in the critical angle produced by changes in the refractive index of the ink; and an ink concentration determining device adapted to determine the concentration of the ink from the measurement by the sensor.

7. An ink concentration measuring and control system comprising:

an interface between an ink and an optically transparent material, wherein the transparent material has an index of refraction higher than an index of refraction of the ink;

a light measurement device adapted to measure the attenuated total reflection of light off the interface between the ink and the transparent material at a range of reflection angles that includes at least a critical angle for the attenuated total reflection;

a reference device adapted to receive light reflected from the interface at angles significantly greater than the critical angle for the attenuated total reflection so that amplitude of the reflected light is not affected by changes in the critical angle produced by changes in the refractive index of the ink; and an output device adapted to produce an ink concentration related output from the attenuated total reflection measured by the measurement device.

* * * * *